United States Patent
Zeller et al.

(10) Patent No.: US 11,998,361 B2
(45) Date of Patent: Jun. 4, 2024

(54) IMAGING APPARATUS, LOCAL COIL AND METHOD FOR CORRECTING A PATIENT MOVEMENT

(71) Applicant: Siemens Healthcare GmbH, Erlangen (DE)

(72) Inventors: Mario Zeller, Erlangen (DE); David Grodzki, Erlangen (DE)

(73) Assignee: Siemens Healthineers AG, Erlangen (DE)

(*) Notice: Subject to any disclaimer, the term of this patent is extended or adjusted under 35 U.S.C. 154(b) by 171 days.

(21) Appl. No.: 17/680,097

(22) Filed: Feb. 24, 2022

(65) Prior Publication Data
US 2022/0280117 A1 Sep. 8, 2022

(30) Foreign Application Priority Data
Mar. 4, 2021 (DE) .................. 102021202118.2

(51) Int. Cl.
*A61B 5/05* (2021.01)
*A61B 5/00* (2006.01)
(Continued)

(52) U.S. Cl.
CPC .............. *A61B 5/721* (2013.01); *A61B 5/004* (2013.01); *A61B 5/055* (2013.01); *A61B 5/1114* (2013.01);
(Continued)

(58) Field of Classification Search
CPC ......... A61B 5/721; A61B 5/004; A61B 5/055; A61B 5/1114; A61B 5/7289; A61B 5/7292; A61B 2562/0219; A61B 2562/164
See application file for complete search history.

(56) References Cited

U.S. PATENT DOCUMENTS

2005/0107685 A1* 5/2005 Seeber .................. A61B 5/721
600/595
2009/0129556 A1 5/2009 Ahn
(Continued)

FOREIGN PATENT DOCUMENTS

DE 102014201585 A1 7/2015
WO 2009067428 A1 5/2009

OTHER PUBLICATIONS

Chung et al:"A simple 5-DoF MR-compatible motion signal measurement system"Behav Res (2011) 43:897-901 DOI 10.3758/s13428-011-0082, Published online: Apr. 13, 2011 # Psychonomic Society, Inc. 2011.

*Primary Examiner* — Joel F Brutus
(74) *Attorney, Agent, or Firm* — Banner & Witcoff Ltd.

(57) ABSTRACT

The disclosure relates to an imaging apparatus for acquiring image data from a diagnostically-relevant body region of a patient comprising a sensor and a correction unit, wherein the at least one sensor is embodied to output a signal containing information on movement of the diagnostically relevant body region of the patient and the correction unit is embodied to receive the signal from the at least one sensor, and to apply a correction method in dependence on the signal to reduce the influence of the movement of the diagnostically relevant body region of the patient on an imaging examination. The disclosure further relates to a local coil for acquiring magnetic resonance signals in a frequency and power range of a magnetic resonance measurement, and a method for correcting patient movement.

16 Claims, 7 Drawing Sheets

(51) Int. Cl.
    *A61B 5/055*   (2006.01)
    *A61B 5/11*    (2006.01)
    *G01R 33/565*  (2006.01)
(52) U.S. Cl.
    CPC .......... *A61B 5/7289* (2013.01); *A61B 5/7292* (2013.01); *G01R 33/56509* (2013.01); *A61B 2562/0219* (2013.01); *A61B 2562/164* (2013.01)

(56) References Cited

U.S. PATENT DOCUMENTS

| | | | |
|---|---|---|---|
| 2014/0128721 A1* | 5/2014 | Forthmann | A61B 5/1128 600/407 |
| 2015/0208946 A1 | 7/2015 | Popescu | |
| 2020/0038160 A1* | 2/2020 | Hornung | B33Y 80/00 |

* cited by examiner

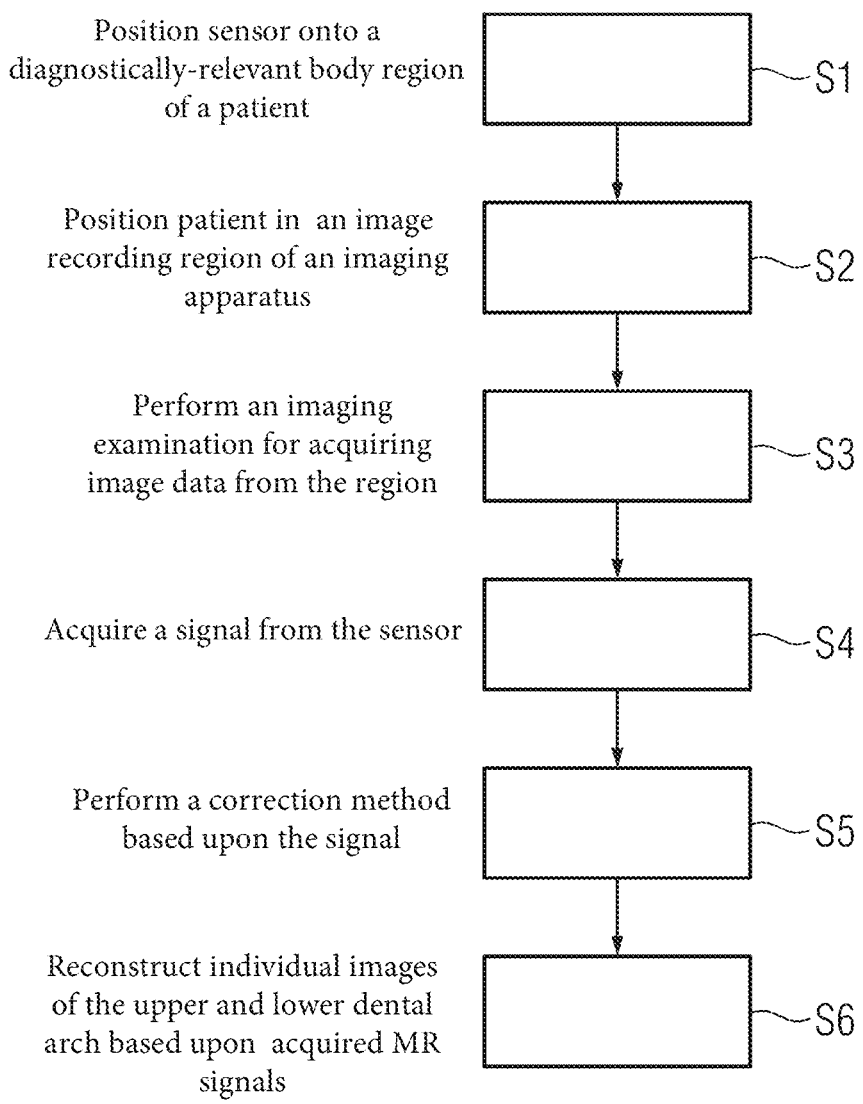

IMAGING APPARATUS, LOCAL COIL AND METHOD FOR CORRECTING A PATIENT MOVEMENT

CROSS-REFERENCE TO RELATED APPLICATIONS

The present application claims the benefit of the filing date of Germany patent application no. DE 10 2021 202 118.2, filed on Mar. 4, 2021, the contents of which are incorporated herein by reference in their entirety.

TECHNICAL FIELD

The disclosure relates to an imaging apparatus for acquiring image data from a diagnostically-relevant patient body region comprising at least one sensor and a correction unit, wherein the correction unit is embodied to receive a signal from the at least one sensor and to apply a correction method in dependence on the signal in order to reduce the influence of a movement of the diagnostically-relevant patient body region on an imaging examination. The disclosure further relates to a local coil for acquiring magnetic resonance signals in a frequency and power range of a magnetic resonance measurement comprising at least one sensor and a method for correcting a patient movement during an imaging examination by means of an imaging apparatus with at least one sensor and a correction unit.

BACKGROUND

Patient movement represents a key challenge in imaging examination methods. Depending on a diagnostically-relevant patient body region and an imaging examination to be performed, the patient movement can significantly impair a quality of acquired images and thus limit diagnosis or render diagnosis impossible. In such cases, imaging examinations are frequently repeated resulting in a corresponding increase in the amount of time required.

SUMMARY

There are various methods for dealing with the patient movement. These include, for example, a use of sequence-inherent navigator measurements, pilot tone acquisition, retrospective correction methods and external sensors, such as, for example, cameras or other optical measuring methods. Furthermore, there are so-called motion gating methods in which recordings are only performed in certain respiratory or ECG states. In this case, the time of image acquisition is typically determined by means of a navigator measurement or an imaging optical sensor. In addition, it is possible to use methods that are inherently robust with respect to movements (for example radial imaging sequences), have the shortest possible measurement duration or comprise a number of averaging operations in order to reduce the influence of movement. It is also conceivable for different methods to be used simultaneously which may result in disadvantages with respect to resolution and/or a duration of the imaging examination. Further, many of the methods named require complex technology for implementation and/or high computing capacity.

It is an object of the disclosure to provide a cost-effective alternative for reducing an influence of the patient movement on image data from an imaging examination.

This object is achieved according to the disclosure by the subject matter of the embodiments as described throughout the disclosure and the claims.

The imaging apparatus according to the disclosure for acquiring image data from a diagnostically-relevant patient body region comprises at least one sensor and a correction unit.

An imaging apparatus can be configured to record diagnostic images containing structural and/or functional information on the diagnostically-relevant patient body region. The recoded images may have three-dimensional information on the diagnostically-relevant patient body region. Examples of such imaging apparatuses include magnetic resonance imaging systems, computed tomography systems, positron emission tomography systems, single photon emission computed tomography systems, and the like.

A diagnostically-relevant patient body region can be any body region of the patient, such as, for example, an arm, a hand, a head, a shoulder, a chest, a leg, a foot, a hip or the like. The diagnostically relevant body region can e.g. exhibit increased mobility compared to the rest of the patient's body and/or a joint. The diagnostically-relevant patient body region may represent e.g. a patient's knee joint, wrist, jaw joint, ankle, shoulder joint or head.

The at least one sensor is embodied to (i.e. configured to) output a signal containing information on movement of the diagnostically-relevant patient body region. The at least one sensor of the imaging apparatus is a non-imaging sensor. In this case, an imaging sensor is e.g. understood to mean a sensor based on an image of a patient and/or an object in an examination space of the imaging apparatus, for example by utilizing a photoelectric effect. Therefore, a fiber optic sensor in which a change to a parameter of the light used is used as a measuring principle is therefore not considered to be an imaging sensor. The at least one sensor can include a measurement-sensitive part and a measuring transducer that converts an acquired input variable into an output variable in accordance with a predetermined relationship. However, it is likewise conceivable for the at least one sensor to include only one measurement-sensitive sensor. In this case, the signal output by the least one sensor can be reshaped or converted by means of a separate measuring transducer and/or a computing unit of the imaging apparatus.

The at least one sensor can use any non-imaging measuring principle suitable for ascertaining information on movement of the diagnostically-relevant patient body region. It is conceivable for the at least one sensor to be positioned for this purpose in a position according to the application on the diagnostically relevant body region. When positioned according to the application, the at least one sensor may be deformed, moved, or exposed to force as a result of a movement of the diagnostically relevant body region. Accordingly, the measuring principle can be suitable for ascertaining and/or quantifying a deformation of the at least one sensor, a movement of the at least one sensor and/or an exertion of force on the at least one sensor. The at least one sensor can be positioned on the diagnostically relevant body region in such a way that the deformation of the at least one sensor, the movement of the at least one sensor, the force on the at least one sensor and/or another measured variable of the at least one sensor is dependent on the movement of the diagnostically relevant body region. This may mean that the signal from the at least one sensor has a direct or indirect correlation with the movement of the diagnostically-relevant patient body region. In the case of indirect correlation, there can be a non-linear relationship between the change in the signal from the at least one sensor and the movement of the diagnostically-relevant patient body region. Further, in the case of indirect correlation, it may be necessary to acquire a second signal from a second, non-imaging sensor or signals from further non-imaging sensors in order to ascertain or quantify the movement of the diagnostically-relevant patient body region. Furthermore, indirect correlation may mean that the signal from the at least one sensor is proportional to a measured variable, such as, for example, a force, a pressure, and/or a signal property that is not proportional to a change in a spatial location of the diagnostically-relevant patient body region.

Examples of suitable sensors are gyro sensors, acceleration sensors, pressure sensors, Hall sensors, distance sensors, and the like. A further example is a bending sensor based on a fiber-optic sensor embodied to ascertain pressure-induced bending losses in dependence on a change in transmission in a glass fiber of the bending sensor.

It is conceivable for the at least one sensor to be mechanically connected to a support element embodied to hold the at least one sensor in the position according to the application on the diagnostically-relevant patient body region. Examples of suitable support elements are eyeglasses, a belt, a glove, a shoe, or the like. It is further conceivable for the support element to have an adaptation element that connects the support element in a force-fitting manner and/or in a form-fitting manner to a body or a body region of the patient. In addition, the support element and/or the at least one sensor can also be connected to the patient's body using an adhesive element. The signal from the at least one sensor comprises information on the movement of the diagnostically-relevant patient body region that is indicative of the extent of the deformation, movement, and/or force. For example, the information on the movement of the diagnostically relevant body region can be indicative of the extent or order of magnitude of the deformation of the at least one sensor, the movement of the at least one sensor and/or the force exerted on the at least one sensor.

The correction unit is embodied to receive the signal from the at least one sensor and to apply a correction method in dependence on the signal in order to reduce an influence of the movement of the diagnostically-relevant patient body region on an imaging examination. The correction unit can be designed as part of a control unit and/or a computing unit of the imaging apparatus. It is in e.g. conceivable for the correction unit to be embodied to coordinate a sequence and/or image data acquisition of an imaging examination and/or to influence a reconstruction of image data from the imaging examination in dependence on the signal from the at least one sensor. The correction unit can furthermore include an image processing unit embodied to reconstruct images in dependence on image data acquired from the imaging examination.

The provision of an imaging apparatus according to the disclosure enables the implementation of a cost-effective alternative to imaging systems for motion correction, such as, for example, camera-based systems to take account of a patient movement. For instance, imaging systems require computationally intensive image processing algorithms with a corresponding computing structure, which can advantageously be avoided when using non-imaging sensors.

In one embodiment, the imaging apparatus according to the disclosure is embodied as a magnetic resonance imaging system that includes a local coil. The local coil can, for example, be embodied as a lay-on coil or include a support element that fixes the local coil on the patient's body. It is further conceivable for the local coil to be embodied as a cage or a hollow body of any shape which at least partially encloses the periphery of the diagnostically relevant body region.

The local coil is positioned in a position according to the application on the diagnostically-relevant patient body region and embodied to receive magnetic resonance signals in a frequency and power range of a magnetic resonance measurement. Magnetic resonance signals can be considered to be electromagnetic waves with a frequency between 1 and 500 MHz or a smaller subset of this frequency such as e.g. between 10 and 300 MHz. The power range of magnetic resonance signals can, for example, be a few $\mu W$ to multiple mW. It is further conceivable for the local coil also to be embodied to excite nuclear spins in the diagnostically-relevant patient body region. Depending on a static magnetic field (B0 magnetic field) of the magnetic resonance imaging system, a transmission power of the local coil can lie in a power range of a few watts to multiple kilowatts.

The local coil comprises the at least one sensor, which is designed as an acceleration sensor, a gyro sensor, and/or a Hall sensor. When the local coil is positioned according to the application, the at least one sensor can be positioned on the diagnostically-relevant patient body region in such a way that a movement of the diagnostically relevant body region causes a corresponding movement of the at least one sensor along a movement trajectory. The at least one sensor may be embodied to ascertain the movement trajectory indirectly in the form of an acceleration and/or a rotational speed and to transmit it to the correction unit.

In one embodiment, at least one sensor of the magnetic resonance imaging system is embodied as a Hall sensor. The Hall sensor may be configured to use or take into account the existing static magnetic field and/or a dynamic magnetic field, such as, for example, a magnetic gradient field or a B1 magnetic field for ascertaining the information on the movement of the diagnostically-relevant patient body region.

In a further embodiment, the at least one sensor and/or the local coil includes an electronic circuit embodied to transmit the signal from the at least one sensor together with an acquired magnetic resonance signal from the local coil to the magnetic resonance imaging system. It is conceivable for the signal to be transmitted in the form of digital data via an electrical connection line that electrically connects the local coil to the magnetic resonance imaging system. However, it is also conceivable for the electronic circuit to comprise a modulation unit, which modulates the signal from the at least one sensor onto the acquired magnetic resonance signal from the local coil. In this case, the magnetic resonance imaging system may include a demodulation unit embodied to separate the signal from the at least one sensor from the acquired magnetic resonance signals by means of demodulation. The electronic circuit can further be embodied to transmit the signal from the at least one sensor and/or the acquired magnetic resonance signals wirelessly to the magnetic resonance imaging system. The electronic circuit can further be embodied to transmit the signal from the at least one sensor as an electromagnetic wave in the frequency and power range of a magnetic resonance signal so that the signal can be received by a receiving unit of the magnetic resonance imaging system. The signal from the at least one sensor may differ from the acquired magnetic resonance signal in terms of a frequency, an amplitude, and/or a bandwidth in order to facilitate a differentiation or separation of the signal from the acquired magnetic resonance signal.

The provision of a local coil with at least one sensor enables the implementation of a particularly compact solution for ascertaining movement of the diagnostically-relevant patient body region, which advantageously reduces the number of electronic components in an image recording region of the magnetic resonance imaging system. Further, the signal from the at least one sensor can be transmitted to the magnetic resonance imaging system together with the acquired magnetic resonance signal from the local coil. This advantageously enables additional connection lines for the at least one sensor to be avoided.

According to a further embodiment, the imaging apparatus includes a transmitter-receiver arrangement comprising the at least one sensor, wherein a transmitter of the transmitter-receiver arrangement is embodied to transmit a reference signal and wherein a receiver of the transmitter-receiver arrangement is embodied to receive the reference signal. The transmitter and/or the receiver are positioned in a position according to the application in a patient receiving region of the imaging apparatus in such a manner that a signal property of the reference signal between the transmitter and the receiver is correlated with the movement of the diagnostically-relevant patient body region. This may mean that the transmitter or the receiver is positioned in a position according to the application on the diagnostically-relevant patient body region in such a manner that a distance between the transmitter and the receiver is correlated with the movement of the diagnostically-relevant patient body region. For example, the transmitter can be positioned on the diagnostically-relevant patient body region while the receiver is mechanically connected to a static component of the imaging apparatus. The receiver can e.g. be positioned on a wall of a patient tunnel of the imaging apparatus. In a further example, the receiver is positioned on the diagnostically-relevant patient body region while the transmitter is mechanically connected to the imaging apparatus. The at least one sensor may be positioned with the transmitter or the receiver on the diagnostically-relevant patient body region. It is furthermore conceivable for the transmitter and the receiver to be mechanically connected to a static component of the imaging apparatus or on the diagnostically-relevant patient body region. This may mean that the reference signal emitted by the transmitter is reflected by the diagnostically-relevant patient body region or the static component of the imaging apparatus before being received by the receiver. Thus, movement of the diagnostically-relevant patient body region can cause a change in a signal property of the reference signal, such as, for example, a delay time, a delay time difference, a degree of reflection or a degree of refraction, which is indirectly correlated with the movement of the diagnostically-relevant patient body region. A patient receiving region can comprise any volume of the imaging apparatus suitable for recording, supporting and/or positioning the patient according to the application during an imaging examination.

The imaging apparatus is embodied to ascertain the movement of the diagnostically-relevant patient body region by means of the at least one sensor in dependence on the received reference signal. This may mean that the at least one sensor is embodied to ascertain the distance between the transmitter and the receiver in dependence on the received reference signal. However, it is likewise conceivable for a computing unit of the imaging apparatus and/or a separate signal processing unit to be embodied to ascertain the movement of the diagnostically-relevant patient body region in dependence on the signal from the at least one sensor. A reference signal can be an electromagnetic wave, such as, for example, an ultrasound signal or a radio-frequency electromagnetic signal in the frequency and power range of a magnetic resonance measurement. For example, the transmitter can be embodied as an ultrasonic transmitter embodied to transmit an ultrasound signal to the receiver. Accordingly, the receiver can be designed as an ultrasonic receiver. The at least one sensor can be embodied to determine a distance between the transmitter and the receiver or a distance between the diagnostically relevant body region and a static component of the imaging apparatus in dependence on the signal property of the reference signal and/or to output a signal correlated with the signal property.

It is furthermore conceivable for the receiver of the transmitter-receiver arrangement and the at least one sensor to be embodied as a receiving unit of a magnetic resonance imaging system. In this case, the transmitter can comprise an antenna element embodied to excite a predetermined signal volume positioned on the diagnostically-relevant patient body region. The excited signal volume can, for example, constitute a tissue on the diagnostically-relevant patient body region or a water volume positioned with the transmitter on the patient. Further, the antenna element of the transmitter can also be embodied to output a reference signal that can be directly acquired by the receiving unit of the magnetic resonance imaging system. The reference signal from the transmitter or the excited signal volume may lie within a frequency and power range of a magnetic resonance measurement. In this case, the reference signal can differ from an acquired magnetic resonance signal in terms of a frequency, an amplitude and/or a bandwidth.

The use of an ultrasound-based transmitter-receiver arrangement advantageously enables cost-effective implementation of motion detection. The provision of a transmitter that excites a signal volume on the diagnostically-relevant patient body region enables a receiving unit of a magnetic resonance imaging system to be used as a receiver. This can advantageously reduce the number of electronic components in the image recording region.

In one embodiment of the imaging apparatus according to the disclosure, the at least one sensor comprises a flexible sensor element positioned in a position according to the application on the diagnostically-relevant patient body region and configured to be deformed as a result of a movement of the diagnostically-relevant patient body region. The flexible sensor element can include an elastically or plastically deformable material. The elastically or plastically deformable material may be embodied to be fitted onto an external contour of the diagnostically-relevant patient body region. Examples of suitable materials include plastics, such as, for example, polyethenes, polyamides, polyesters, and polyurethanes, but also natural substances such as rubber. It is conceivable for at least one measurement-sensitive part of the at least one sensor to be electrically and/or mechanically connected to the flexible sensor element and/or embedded in the flexible sensor element. The measurement-sensitive part of the at least one sensor can, for example, be a piezoelectric element, a piezoresistive element, but also a capacitive or inductive pressure sensor. In one example, the at least one sensor is embodied as a strain gauge in which a measuring grid foil is embedded in the flexible sensor element. In this case, the flexible sensor element is positioned on a patient's knee joint such that at least one first section of the flexible sensor element is positioned on part of a patient's thigh, while a second section of the flexible sensor element is positioned on a patient's lower leg. The flexible sensor element is correspondingly deformed when the knee joint moves.

In a further embodiment, the at least one sensor of the magnetic resonance imaging system takes the form of a fiber optic sensor. The fiber optic sensor can be embodied to ascertain deformation of the flexible sensor element as a result of a change in transmission of glass fibers connected to the flexible sensor element. A fiber optic sensor can comprise a photodiode and a glass fiber, wherein the glass fiber is connected to the flexible sensor element such that, when the flexible sensor element is deformed, the glass fiber is also deformed. The photodiode may be embodied to measure an intensity of light passed through the glass fiber at a defined exit point of the glass fiber. For example, a light-emitting diode (LED) that couples light into the glass fiber is arranged at one end of the glass fiber and the photodiode that measures light exiting at the other end is arranged at the other end of the glass fiber. The intensity of the light acquired by means of the photodiode can e.g. be a measure of the deformation of the flexible sensor element.

The imaging apparatus is embodied to ascertain information on the movement of the diagnostically-relevant patient body region by means of the at least one sensor in dependence on the deformation of the flexible sensor element. The at least one sensor with the flexible sensor element can obviously be positioned on different body regions. For example, the at least one sensor can be positioned on a jaw region, a hand region, a hip region, a foot region, a shoulder region, or the like such that a movement of the corresponding body region causes deformation of the flexible sensor element. The measurement-sensitive part of the at least one sensor can be embodied to acquire the extent or order of magnitude of the deformation of the flexible sensor element. The at least one sensor may be embodied to provide a signal correlated with the extent or order of magnitude of the deformation.

The provision of a sensor according to the disclosure with a flexible sensor element advantageously enables the implementation of a particularly cost-effective solution for ascertaining a patient movement during the imaging examination.

In a further embodiment, the imaging apparatus according to the disclosure further includes a support element, which is mechanically connected to the flexible sensor element and is configured to hold the flexible sensor element in the position according to the application on the diagnostically-relevant patient body region. The support element can be designed according to one of the above-described embodiments. The support element may include an adaptation element, such as, for example, a belt buckle, a Velcro element, a latching element, a zipper, a clamping element, or the like, embodied to adapt the support element individually to a patient's body region and/or to fix it to the patient's body region. The support element may be positioned on a patient's body such that the flexible sensor element is held in the position according to the application on the diagnostically relevant body region. In this case, the support element can be connected to the flexible sensor element and/or the at least one sensor in a force-fitting manner, form-fitting manner and/or with a material bond.

The support element and the flexible sensor element are configured to be positioned relative to one another upon movement of the diagnostically-relevant patient body region with deformation of the flexible sensor element, wherein the imaging apparatus is embodied to ascertain information on the movement of the diagnostically-relevant patient body region by means of the at least one sensor in dependence on the relative movement of the support element and the flexible sensor element. When positioned according to the application, the support element and the flexible sensor element may be positioned on opposite body regions of a patient's joint so that, when the joint moves, the support element and the flexible sensor element are moved relative to one another with deformation of the flexible sensor element. However, it is likewise conceivable for the support element to be substantially positioned on a joint or another movable patient body region and connected to a plurality of flexible sensor elements, which are deformed and moved relative to the support element upon different movements of the body region.

The provision of a support element advantageously enables the at least one sensor with the flexible sensor element to be positioned in a robust and reproducible manner on the diagnostically relevant body region. This can advantageously increase the quality of the ascertaining of the patient movement.

According to one embodiment, the imaging apparatus according to the disclosure further includes a second support element connected to the support element by means of the flexible sensor element. The second support element can be designed according to one of the above-described embodiments and connected to the flexible sensor element.

The support element and the second support element are positioned in a position according to the application on opposite body regions on a patient's joint, wherein the flexible sensor element is configured to be deformed as a result of movement of the joint, wherein the imaging apparatus is embodied to ascertain the movement of the joint by means of the at least one sensor in dependence on the deformation of the flexible sensor element.

Positioning the support element and the second support element on opposite body regions on a patient's joint enables the at least one sensor with the flexible sensor element to be positioned in a particularly precise and reproducible manner on the diagnostically relevant body region. Furthermore, the ascertaining of the patient movement by means of the at least one sensor can advantageously be supplemented by a distance measurement between the support element and the second support element. Such a distance measurement can, for example, be performed by means of a transmitter-receiver arrangement according to an above-described embodiment.

In one embodiment, the flexible sensor element is positioned in the position according to the application on a dental arch of the patient and embodied to be deformed as a result of movement of a lower jaw of the patient, wherein the imaging apparatus is embodied to ascertain a movement of the lower jaw by means of the at least one sensor in dependence on the deformation of the flexible sensor element. It is conceivable for the flexible sensor element to be designed as a bite splint or bite piece positioned in a position according to the application in an oral cavity of the patient between the lower jaw and the upper jaw. The flexible sensor element may be embodied to be deformed when the upper jaw and the lower jaw are brought together. In this case, the at least one sensor can ascertain movement of the lower jaw in dependence on the deformation of the flexible sensor element.

In a further embodiment, the support element takes the form of a bite splint and is positioned in a position according to the application on a dental arch of the patient. In this case, the support element can e.g. be shaped to follow a contour and/or a shape of the dental arch and include a recess for the patient's tongue. As described above, the flexible sensor element may be connected to the support element on a first section and extends in the direction of an opposite dental arch. The support element is, for example, positioned on the upper dental arch of the upper jaw. On the other hand, the at least one second section of the flexible sensor element is positioned on the lower dental arch of the lower jaw so that the flexible sensor element is deformed upon movement of the lower jaw. It is likewise conceivable for a second support element to be positioned on the patient's lower dental arch. In this case, the support element on the upper dental arch and the second support element on the lower dental arch may be connected by means of the flexible sensor element so that a relative movement of the support element and the second support element as a result of a movement of the lower jaw causes a deformation of the flexible sensor element. In this case, deformation of the flexible sensor element can take the form of elongation, compression, torsion, bending, or the like.

In a further embodiment, at least the support element includes at least one antenna element configured to receive magnetic resonance signals in a frequency and power range of a magnetic resonance measurement from the patient's jaw region. The support element may be embodied to hold the at least one antenna element in a position according to the application on a dental arch of the patient. In this case the support element can e.g. be a local coil.

The provision of a sensor with a flexible sensor element for positioning in the patient's oral cavity advantageously enables a relative movement between the patient's upper jaw and lower jaw during the imaging examination to be ascertained and used by the correction unit. This advantageously enables the influence of movements of the patient's jaw region on the imaging examination to be avoided.

In a preferred embodiment, the imaging apparatus according to the disclosure is embodied as a magnetic resonance imaging system, wherein the magnetic resonance imaging system includes a local coil comprising the sensor with the flexible sensor element, wherein the local coil is embodied to receive magnetic resonance signals in a frequency and power range of a magnetic resonance measurement. The local coil can include a support element embodied to hold the local coil and/or the at least one sensor in a position according to the application on the diagnostically-relevant patient body region. As described above, the local coil can further include at least one antenna element embodied to receive magnetic resonance signals from the diagnostically-relevant patient body region.

At least one section of the local coil with the flexible sensor element is reversibly deformable, wherein the at least one sensor is embodied to output a signal correlated with the deformation of the flexible sensor element. It is conceivable for the local coil to include a plurality of elements connected by means of flexible sensor elements. Thus, the local coil can be reversibly deformable on sections with flexible sensor elements and can adapt to patient movement. The at least one sensor is correspondingly embodied to ascertain or quantify the deformation of the flexible sensor elements.

In one example, the local coil includes a support element positioned on the patient's lower dental arch. The support element may take the form of a bite splint embodied to hold at least one antenna element in a position according to the application on the patient's lower dental arch.

In a further example, the local coil is embodied as a lay-on coil positioned in a position according to the application on a patient's knee joint. In this embodiment, the local coil may include a plurality of flexible sensor elements which are deformed when the knee joint moves. It is conceivable for the local coil's own weight to be sufficient to hold the local coil in the position according to the application on the knee joint such that deformation of the flexible sensor elements can take place as a result of movement of the knee joint. However, it is likewise conceivable for at least one section of the local coil to be attached to a patient's body region, such as, for example, a thigh and/or a lower leg by means of a support element in order to support deformation of the flexible sensor elements upon movement of the knee joint. Obviously, the local coil can be embodied to be positioned on any further body regions of the patient in order to detect a patient movement.

The provision of a local coil according to the disclosure with the at least one sensor advantageously enables the acquisition of magnetic resonance signals from the diagnostically relevant body region to be combined with the ascertaining of the movement of the diagnostically relevant body region. Further, the local coil according to the disclosure can include a plurality of antenna elements which can be positioned relative to one another by means of the flexible sensor elements. This advantageously also enables the acquisition of magnetic resonance signals from the diagnostically relevant body region upon patient movement, which signals are corrected in dependence on the signal from the at least one sensor by means of the correction method.

The method according to the disclosure for correcting patient movement during an imaging examination by means of an imaging apparatus with at least one sensor and a correction unit, wherein the at least one sensor is a non-imaging sensor and is embodied to output a signal containing information on movement of the diagnostically-relevant patient body region, comprises the steps:

positioning (S1) the at least one sensor on a diagnostically-relevant patient body region, positioning (S2) the patient in an image recording region of the imaging apparatus, performing (S3) the imaging examination for acquiring image data from the diagnostically-relevant patient body region, acquiring (S4) the signal from the at least one sensor and performing (S5) a correction method by means of the correction unit in dependence on the signal from the at least one sensor, wherein the correction method reduces an influence of the movement of the diagnostically-relevant patient body region on the imaging examination.

The imaging apparatus, the at least one sensor, and the correction unit may be designed (i.e. configured) according to an above-described embodiment. An imaging examination can comprise preparation for acquiring image data, acquisition of image data, but also the creation or reconstruction of images in dependence on the acquired image data by means of an imaging apparatus.

The positioning of the at least one sensor can comprise laying-on, applying, placing, attaching and/or securing the at least one sensor on the diagnostically-relevant patient body region. For example, the at least one sensor can be connected to a surface of the diagnostically relevant body region by means of an adhesive element. However, it is likewise conceivable for the at least one sensor to be connected to a support element, such as, for example, eyeglasses, a glove, a stocking, or any other item of clothing, which is matched to the diagnostically relevant body region and/or can be adapted thereto. Further, the support element can be designed according to an above-described embodiment. In a preferred embodiment, the at least one sensor is connected to a local coil of a magnetic resonance imaging system. Accordingly, the at least one sensor can be positioned in the position according to the application when positioning the local coil on the diagnostically-relevant body region.

The patient may be positioned in an image recording region of an imaging apparatus by means of a patient table.

The patient table can be designed to position the diagnostically relevant body region in the image recording region of the imaging apparatus or in an isocenter of a magnetic resonance imaging system. It is conceivable for testing, calibration and/or function monitoring of the at least one sensor and/or a transmitter-receiver arrangement according to an above-described embodiment to be performed during the positioning of the patient in an image recording region and/or the positioning of the at least one sensor on the diagnostically relevant body region.

The imaging examination for acquiring image data from the diagnostically-relevant patient body region can, for example, comprise the performance of a magnetic resonance imaging measurement, a computed tomography measurement, a positron emission tomography measurement, a single photon emission computed tomography measurement or comparable imaging methods.

It is conceivable for the acquisition of the signal from the at least one sensor to take place during preparation for the imaging examination and/or during the performance of the imaging examination. The signal from the at least one sensor can e.g. take place at the same time as or in parallel with the acquisition of magnetic resonance signals and/or photons or X-rays. For example, as described above, movement of the diagnostically relevant body region can be ascertained and/or quantified by means of the at least one sensor during the imaging examination.

The correction method can comprise the application of any method or a plurality of any methods that reduce the influence of patient movement on the imaging examination. In one example, the correction method can comprise the application of motion gating. Motion gating matches the time of acquisition of image data with patient movement, e.g. the signal from the at least one sensor. In this case, the acquisition of image data can be temporarily suspended during patient movement, e.g. movement of the diagnostically-relevant body region. In a further example, the correction method can comprise the adaptation of an imaging parameter of the imaging examination, such as, for example, an imaging volume, an excitation pulse frequency, a pulse width, a beam focus or the like, in dependence on the signal from the at least one sensor. It is furthermore conceivable for the correction method to comprise the reconstruction of an image in dependence on the acquired image data and the signal from the at least one sensor. For example, image data acquired during movement of the diagnostically-relevant patient body region can be ignored during the reconstruction of the image. However, it is likewise conceivable for the correction method to comprise a model and/or a compensation method that enables the reconstruction of image data in dependence on the signal from the at least one sensor.

The use of the signal from the non-imaging sensor according to an above-described embodiment of the imaging apparatus according to the disclosure in the method according to the disclosure enables the influence of the movement of the diagnostically relevant body region on the imaging examination to be advantageously reduced in a particularly cost-effective manner and/or with little computational effort.

In one embodiment of the method according to the disclosure, the acquisition of the signal from the at least one sensor comprises acquiring a second signal from at least one second sensor. In this case, the second sensor is a non-imaging sensor and uses a measuring principle that is different from that of the at least one sensor. The second sensor may be designed according to one of the above-described embodiments. It is furthermore conceivable for the acquisition of the signal from the at least one sensor further to comprise the acquisition of a third signal from a third sensor. The third sensor may also be a non-imaging sensor, which uses a measuring principle that is different from that of the first sensor and/or the second sensor.

The second signal contains information on movement of the diagnostically-relevant patient body region. Like the at least one sensor, the second sensor and/or the third sensor can also be embodied to provide a second signal and/or a third signal dependent on an extent or an order of magnitude of movement of the diagnostically-relevant patient body region or directly or indirectly correlated therewith.

The correction method is performed in dependence on the signal from the at least one sensor and the second signal from the second sensor. It is further conceivable for the performance of the correction method to take place in dependence on the signal from the at least one sensor, the second signal from the second sensor and the third signal from the third sensor.

The use of a plurality of non-imaging sensors advantageously enables the accuracy of the acquisition and/or the quantification of a movement of the diagnostically-relevant patient body region to be increased. Further, with a plurality of sensors, it is advantageously possible to use methods for merging the sensor data in order to increase and/or improve the completeness, consistency, accuracy and/or certainty of the information on the movement of the diagnostically relevant body region.

In a further embodiment of the method according to the disclosure, the performance of the correction method comprises performing at least one of the following methods:
motion gating,
outputting feedback regarding the movement of the diagnostically relevant body region to the patient by means of an output unit,
a prospective and/or retrospective correction method.

Motion gating can take place in accordance with an above-described embodiment of the imaging apparatus according to the disclosure in dependence on the signal from the at least one sensor.

An output unit can be embodied to output visual, acoustic, and/or haptic feedback to the patient. The feedback can e.g. take place in dependence on the information on the movement of the diagnostically-relevant patient body region and/or be correlated with the extent of the movement of the diagnostically relevant body region. Examples of an output unit include a monitor, a projection screen, a touchscreen, a loudspeaker, headphones and/or an active control element that transmits tactile information to the patient. The feedback to the patient may be dependent on the patient movement so that the patient is directly notified of the intensity of his movement. For this purpose, it is also, for example, possible to use force feedback which outputs haptic feedback to the patient, the intensity of which is correlated with the movement of the diagnostically relevant body region. The output of feedback regarding the movement of the diagnostically relevant body region to the patient, advantageously enables the patient to be informed of the movement and to stop or counteract the movement.

In a prospective correction method, imaging parameters can still be adapted during the imaging examination in order to reduce the influence of the movement of the diagnostically relevant body region on the imaging examination. For example, a position and/or orientation of a field of view, slice thickness, pulse width, beam focus, distance of the patient to a radiation source, angulation of the radiation source with respect to the patient or the like can be adapted. For instance, during a magnetic resonance examination, a frequency of an excitation pulse for a next series to be recorded in a k-space can be adjusted in order to correct the influence of a translational movement of the diagnostically-relevant patient body region. Accordingly, it is conceivable for encoded gradient fields to be rotated in order to correct a rotational movement of the diagnostically-relevant patient body region.

A retrospective correction method can e.g. be used for a magnetic resonance imaging measurement. With a retrospective correction method, k-space series can be transferred into an image space before the influence of the movement of the diagnostically relevant body region on the imaging examination is corrected. For example, a translational movement of the diagnostically relevant body region can be corrected by a phase change of the acquired image data. On the other hand, a rotational movement of the diagnostically relevant body region can be corrected by applying non-Cartesian reconstruction methods. The image data can e.g. be transmitted to an image processing algorithm for a retrospective method.

A translational movement and/or a rotational movement of the diagnostically relevant body region may be ascertained by means of the at least one sensor, e.g. the flexible sensor element, according to an above-described embodiment of the imaging apparatus according to the disclosure.

The application of one of the aforementioned correction methods advantageously enables robust and reproducible reduction and/or correction of the influence of the movement of the diagnostically-relevant patient body region on the imaging examination.

In a further embodiment of the method according to the disclosure, the imaging apparatus is embodied as a magnetic resonance imaging system, wherein the local coil is positioned on a jaw region of the patient and a plurality of antenna elements, wherein a first antenna element is positioned on an upper dental arch of the patient and a second antenna element is positioned on a lower dental arch of the patient. For this purpose, the local coil can e.g. be designed according to an above-described embodiment of the imaging apparatus according to the disclosure. It is conceivable for the local coil to have a support element and/or a second support element which hold the first antenna element in a position according to the application on the upper dental arch and the second antenna element in a position according to the application on the lower dental arch. For instance, the at least one sensor can include a flexible sensor element, which is positioned in a position according to the application between the upper dental arch and the lower dental arch and, upon deformation as a result of movement of the lower dental arch, outputs a signal correlated with the extent or order of magnitude of the movement of the lower dental arch.

The performance of the imaging examination comprises receiving magnetic resonance signals from the lower dental arch and the upper dental arch by means of the plurality of antenna elements. During the imaging examination, a signal may be likewise acquired from the at least one sensor in order to perform a correction method in dependence on the signal from the at least one sensor.

The performance of the correction method comprises motion gating, wherein magnetic resonance signals from the lower dental arch and/or the upper dental arch are acquired in dependence on the at least one sensor by means of the local coil. This may e.g. mean that the acquisition of magnetic resonance signals by means of the first antenna element and the second antenna element is temporarily suspended upon movement of the diagnostically relevant body region.

In one embodiment, the method according to the disclosure further comprises the step:

reconstructing individual images of the upper dental arch in dependence on the magnetic resonance signals from the first antenna element and the lower dental arch in dependence on the acquired magnetic resonance signals from the second antenna element and merging the individual images of the upper dental arch and the lower dental arch to form one image in an image space.

It is conceivable for a head of the patient and thus also the upper dental arch of the patient to be fixed or locked during the imaging examination. Thus, movement of the patient's jaw region can be primarily restricted to the lower jaw or the lower dental arch. Upon detection of movement by means of the at least one sensor, the acquisition of magnetic resonance signals by means of the second antenna element can be suspended in a dedicated manner, while the acquisition of magnetic resonance signals by means of the first antenna element can be continued. It is conceivable for the magnetic resonance signals acquired from the first antenna element and the second antenna element to be transmitted to an image processing unit for the reconstruction of a single image of the upper dental arch and a single image of the lower dental arch. The individual images of the upper dental arch and the lower dental arch can then be merged by means of the image processing unit to form one image of the patient's dentition.

The method according to the disclosure enables the acquisition of magnetic resonance signals from a non-moving patient body region, while the acquisition of image data from a moving patient body region is suspended in a dedicated manner Hence, despite the application of motion gating, this advantageously enables the provision of high-quality images of the non-moving patient body region.

In one embodiment of the method according to the disclosure, the imaging apparatus is embodied as a magnetic resonance imaging system with a local coil, wherein the signal from the at least one sensor is modulated onto a magnetic resonance signal acquired by means of the local coil. According to an above-described embodiment of the imaging apparatus, the at least one sensor and/or the local coil can include an electronic circuit which modulates the signal from the at least one sensor onto an acquired magnetic resonance signal from the local coil. Accordingly, the magnetic resonance imaging system can include a demodulation unit which separates the signal from the at least one sensor from the magnetic resonance signal. In this case, the signal from the at least one sensor may differ from the acquired magnetic resonance signal in terms of a frequency, an amplitude, and/or a bandwidth to facilitate a differentiation or separation of the signal from the acquired magnetic resonance signal. It is likewise conceivable for the signal from the at least one sensor to be a digital signal, which is transmitted together with the magnetic resonance signal from the local coil to the magnetic resonance imaging system via a common data bus.

Modulating the signal from the at least one sensor onto the acquired magnetic resonance signal from the local coil advantageously enables the number of the signal lines in an image recording region of the magnetic resonance imaging system to be reduced.

The local coil according to the disclosure for acquiring magnetic resonance signals in a frequency and power range of a magnetic resonance measurement comprises at least one sensor with a flexible sensor element, wherein at least one section of the local coil with the flexible sensor element is reversibly deformable and wherein the at least one sensor is embodied to output a signal correlated with the deformation of the flexible sensor element. The local coil according to the disclosure may be designed according to an above-described embodiment of the imaging apparatus according to the disclosure.

The local coil according to the disclosure advantageously enables the complexity of motion detection to be reduced compared to imaging methods. Further, the sensitivity or accuracy of motion detection can be increased in a simple way by increasing the number of flexible sensor elements and/or local coils according to the disclosure.

The computer program product according to the disclosure can be loaded into a memory unit of a computing unit of an imaging apparatus according to an above-described embodiment and includes program code means for executing a method according to the disclosure according to an above-described embodiment when the computer program product is executed in the computing unit of the imaging apparatus.

The computer program product according to the disclosure enables the method according to the disclosure to be executed quickly, identically repeatedly and robustly. The computer program product is configured such that it can execute the method steps according to the disclosure by means of the computing unit. The computing unit in each case fulfills the requisite conditions, such as, for example, having an appropriate working memory, an appropriate graphics card or an appropriate logic unit so that the respective method steps can be executed efficiently. The computer program product is, for example, stored on a computer-readable medium or held on a network, a server or a cloud from where it can be loaded into the processor of a local computing unit. In this case, the computing unit can be embodied as a stand-alone system component or as part of the imaging apparatus. Furthermore, control information of the computer program product can be stored on an electronically readable data carrier. The control information of the electronically readable data carrier can be designed to perform a method according to the disclosure when the data carrier is used in the computing unit of the imaging apparatus. Examples of electronically readable data carriers are a DVD, a magnetic tape, a USB stick or any other data storage medium on which electronically readable control information, e.g. software, is stored. When this control information is read from the data carrier and transmitted to a control unit and/or the computing unit of the imaging apparatus, all the embodiments according to the disclosure of the described method according to the disclosure can be carried out.

BRIEF DESCRIPTION OF THE DRAWINGS/FIGURES

Further advantages and details of the present disclosure emerge from the exemplary embodiments described below and with reference to the drawings. The drawings show:

FIG. 7 illustrates a flow chart of an embodiment of a method according to the disclosure.

DETAILED DESCRIPTION

Figure 1:
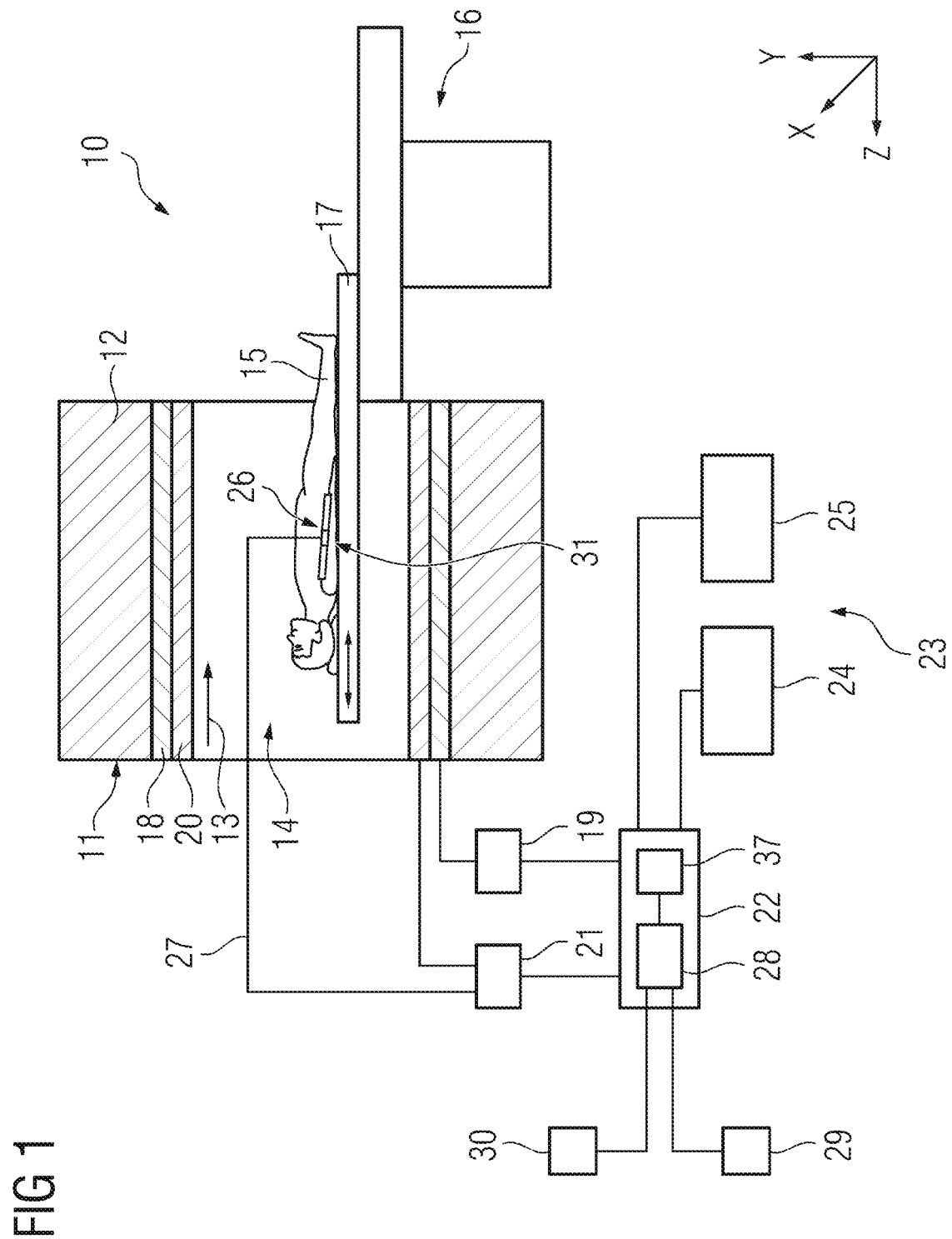
FIG. 1 illustrates a schematic representation of an embodiment of an imaging apparatus according to the disclosure.

FIG. 1 depicts an embodiment of the imaging apparatus 10 according to the disclosure. In the present example, the imaging apparatus 10 takes the form of a magnetic resonance imaging system 10. However, it is likewise conceivable for the imaging apparatus 10 to be designed as a computed tomography system, a positron emission tomography system, a single photon computed tomography system or the like.

The magnetic resonance imaging system 10 comprises a magnet unit 11, which, for example, includes a permanent magnet, an electromagnet or a superconducting main magnet 12 for generating a strong and homogeneous main magnetic field 13 (B0 magnetic field). In addition, the magnetic resonance imaging system 10 comprises a patient receiving region 14 for receiving a patient 15. In the present exemplary embodiment, the patient receiving region 14 is cylindrical in shape and surrounded by the magnet unit 11 in a circumferential direction. However, in principle embodiments of the patient receiving region 14 deviating from this example are also conceivable.

The patient 15 can be positioned in the patient receiving region 14 by means of a patient positioning apparatus 16 of the magnetic resonance imaging system 10. For this purpose, the patient positioning apparatus 16 includes a patient table 17 embodied to be movable within the patient receiving region 14. The magnet unit 11 further includes a gradient coil 18 for generating magnetic gradient fields, which is used for spatial encoding during imaging. The gradient coil 18 is actuated by means of a gradient control unit 19 of the magnetic resonance imaging system 10. The magnet unit 11 can furthermore comprise a radio-frequency antenna which, in the present exemplary embodiment, is embodied as a body coil 20 permanently integrated in the magnetic resonance imaging system 10. The body coil 20 is configured to excite nuclear spins in the main magnetic field 13 generated by the main magnet 12. The body coil 20 is actuated by a radio-frequency unit 21 of the magnetic resonance imaging system 10 and radiates radio-frequency excitation pulses into an image recording region substantially formed by a patient receiving region 14 of the magnetic resonance imaging system 10. The body coil 20 is further embodied to receive magnetic resonance signals and can constitute a receiving unit of the magnetic resonance imaging system 10.

To control the main magnet 12, the gradient control unit 19, and to control the radio-frequency unit 21, the magnetic resonance imaging system 10 includes a control unit 22. The control unit 22 is embodied to control the performance of an imaging sequence of the imaging examination, such as, for example, a GRE (gradient echo) sequence, a TSE (turbo spin echo) sequence or a UTE (ultra-short echo time) sequence. In addition, the control unit 22 comprises a computing unit 28 for evaluating magnetic resonance signals acquired during a magnetic resonance examination. The computing unit 28 of the magnetic resonance imaging system 10 can be embodied to perform a correction method in order to reduce the influence of movement of a diagnostically relevant body region 31 of the patient 15 on the magnetic resonance examination. For this purpose, the computing unit 28 and/or the control unit 22 e.g. include a correction unit 37.

Furthermore, the magnetic resonance imaging system 10 comprises a user interface 23 with a signal connection to the control unit 22. Control information, such as, for example, imaging parameters, but also reconstructed images, can be displayed to a user on a display unit 24, for example on at least one monitor, of the user interface 23. Furthermore, the user interface 23 includes an input unit 25 by means of which parameters of a magnetic resonance examination can be entered by the user.

In the present example, the computing unit 28 is connected to a memory unit 29 of the magnetic resonance imaging system 10 and to a cloud 30. The computing unit 28 can be configured to store data, such as, for example, images and/or image data, on the memory unit 29 and/or the cloud 30 and/or to retrieve this data from the memory unit 29 and/or the cloud 30 by means of a suitable interface. It is e.g. conceivable for the cloud 30 to be embodied to receive acquired image data and acquired signals from at least one sensor, to perform a correction method and to transmit a result of the correction method to the computing unit 29.

The magnetic resonance imaging system 10 can further have a local coil 26, which is positioned in a position according to the application on the diagnostically relevant body region 31 of the patient 15 and acquires magnetic resonance signals from the diagnostically relevant body region 31 of the patient 15 and transmits them to the computing unit 28 and/or the correction unit 37 of the control unit 22. The local coil 26 may have an electrical connection line 27 which provides a signal connection to the radio-frequency unit 21 and the control unit 22. Like the body coil 20, the local coil 26 can also be embodied to excite nuclear spins and receive magnetic resonance signals. For this purpose, the local coil 26 can be actuated by the radio-frequency unit 21. In one example, the local coil 26 takes the form of a lay-on coil positioned on an elbow 31 of the patient 15.

The magnetic resonance imaging system 10 depicted can obviously comprise further components which magnetic resonance imaging systems usually have. Instead of the cylindrical structure, it is likewise conceivable for the magnetic resonance imaging system 10 to have a C-shaped, triangular, or asymmetrical structure of the magnetic-field-generating components. The magnetic resonance imaging system 10 can e.g. be embodied to perform a magnetic resonance examination on a standing or seated patient 15.

Figure 2:
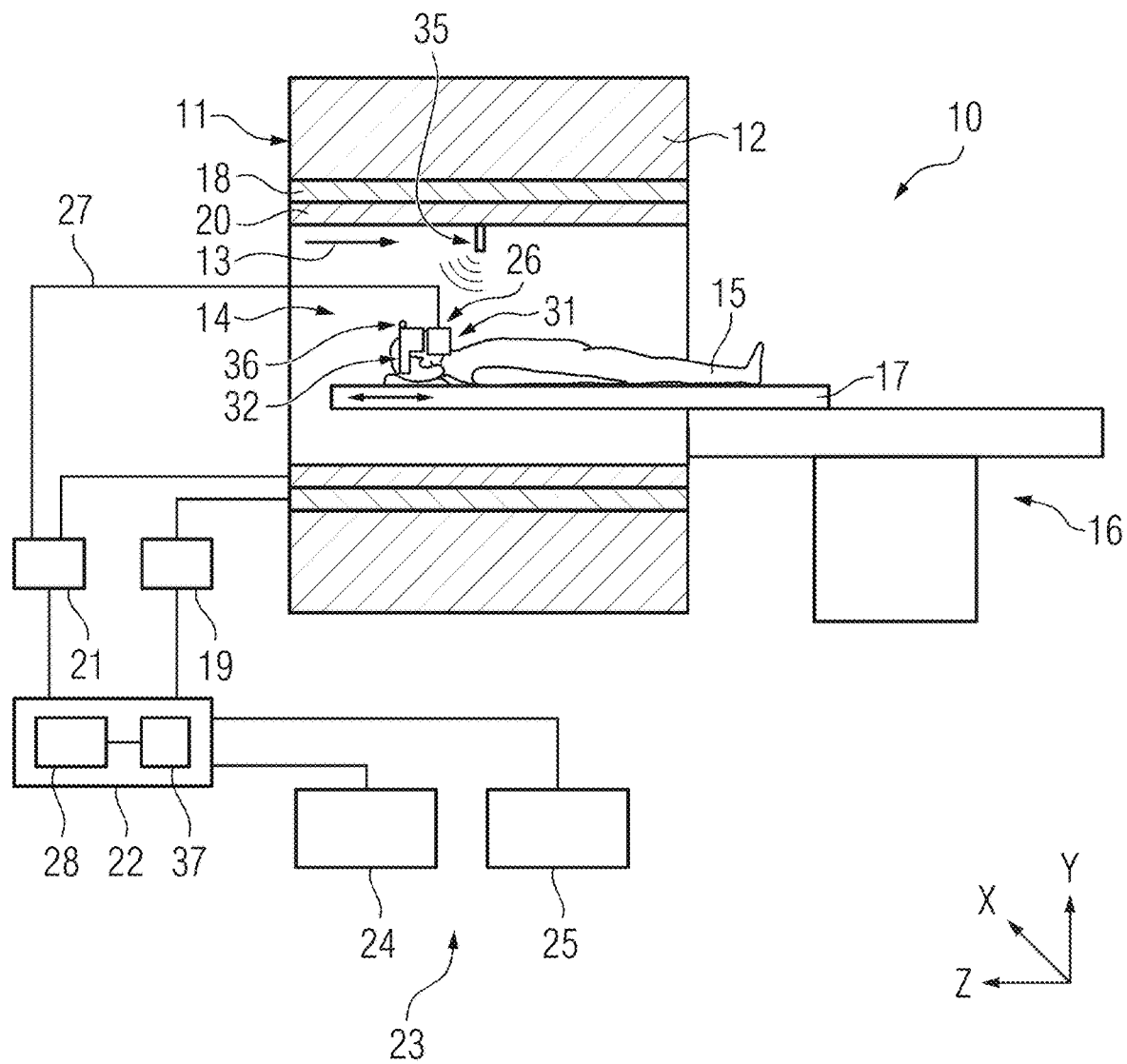
FIG. 2 illustrates a schematic representation of an embodiment of an imaging apparatus according to the disclosure.

FIG. 2 shows an embodiment of the magnetic resonance imaging system 10 with a transmitter-receiver arrangement comprising a transmitter 35 and a receiver 36. In the present example, the receiver 36 is held on the head of the patient 15 by a support element 32, wherein the support element 32 is designed as eyeglasses. The receiver 36 and the support element 32 are positioned on the head of the patient 15 such that a distance between the transmitter 35 and the receiver 36 is at least correlated with movement of the head of the patient 15 in the Y direction and the X direction. The transmitter 35 is embodied to transmit a reference signal to the receiver 36. The receiver 36 and/or the support element 32 may include at least one sensor 33 (not shown), which is embodied to ascertain information on the patient movement 15 in dependence on the received reference signal. The transmitter 35 can e.g. be embodied to transmit an ultrasound signal to the receiver. In the present embodiment, the local coil 26 is positioned on the jaw region 31 of the patient 15. Since movement of the head typically corresponds to movement of the upper jaw, the receiver 36 can also be positioned in the position according to the application in the vicinity of the diagnostically relevant position, such as, for example, the support element 32.

Figure 3:
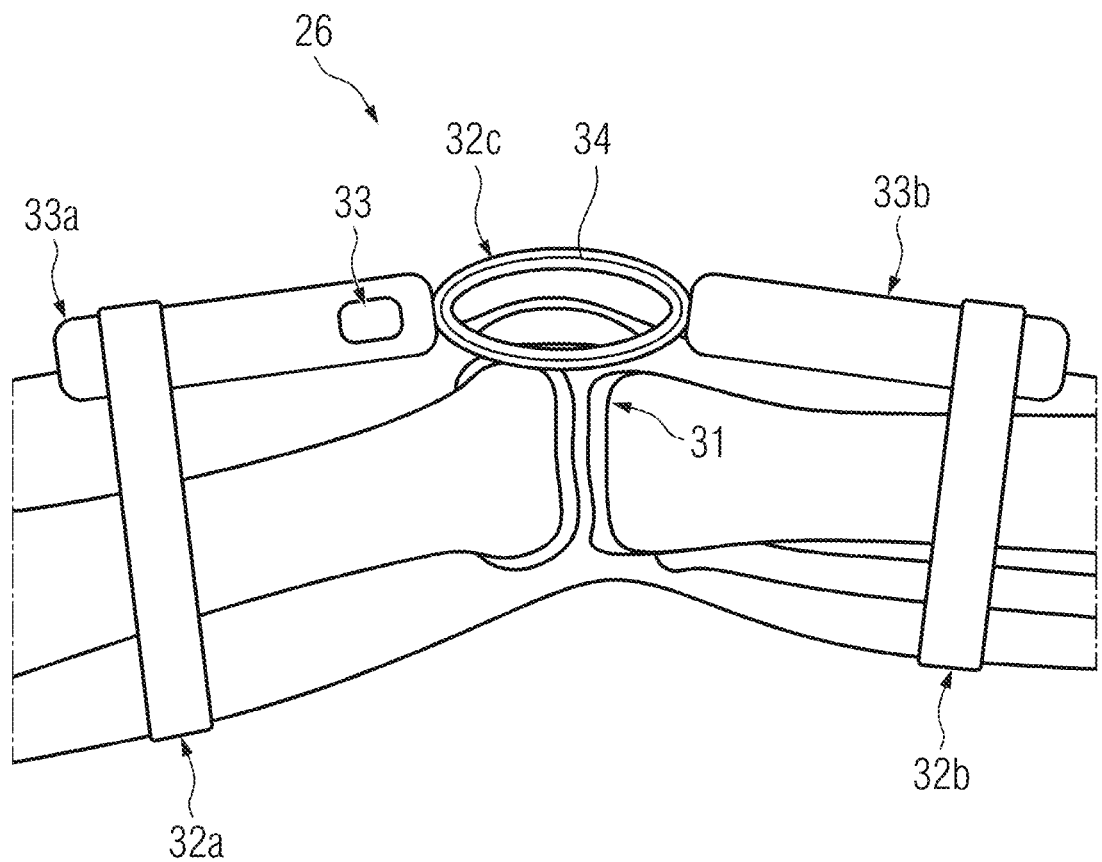
FIG. 3 illustrates an embodiment of a sensor according to the disclosure.

FIG. 3 shows a possible embodiment of the local coil 26 according to the disclosure. In the present example, the local coil 26 is positioned on a knee joint 31 of the patient 15. The local coil 26 has at least one antenna element 34, which is held by the support element 32*c* in the position according to the application on the knee joint 31 of the patient 15. The local coil 26 further includes at least one sensor 33 with flexible sensor elements 33*a* and 33*b*. The flexible sensor elements 33*a* and 33*b* are mechanically connected to the local coil 26.

In the present embodiment, a first section of the flexible sensor elements 33*a* and 33*b* is in each case mechanically connected to the support element 32*c*. A second section of the flexible sensor element 33*a* is positioned on a thigh of the patient 15, while a second section of the flexible sensor element 33*b* is positioned on the lower leg of the patient 15. In this case, the thigh and the lower leg of the patient 15 constitute opposite body regions of the knee joint 31 of the patient 15. It is conceivable for the second sections of the flexible sensor elements 33*a* and 33*b* to be held in a position according to the application by means of the support elements 32*a* and 32*b*. Thus, bending or stretching of the knee joint 31 causes the flexible sensor elements 33*a* and 33*b* to be deformed. The deformation is e.g. correlated with the extent of the bending and/or stretching of the knee joint 31. The at least one sensor 33 may be configured to transmit the extent of the movement of the knee joint 31 in dependence on the deformation of the flexible sensor elements 33*a* and 33*b* to the magnetic resonance imaging system 10 and/or an electronic circuit (not shown) of the local coil 26.

Figure 4:
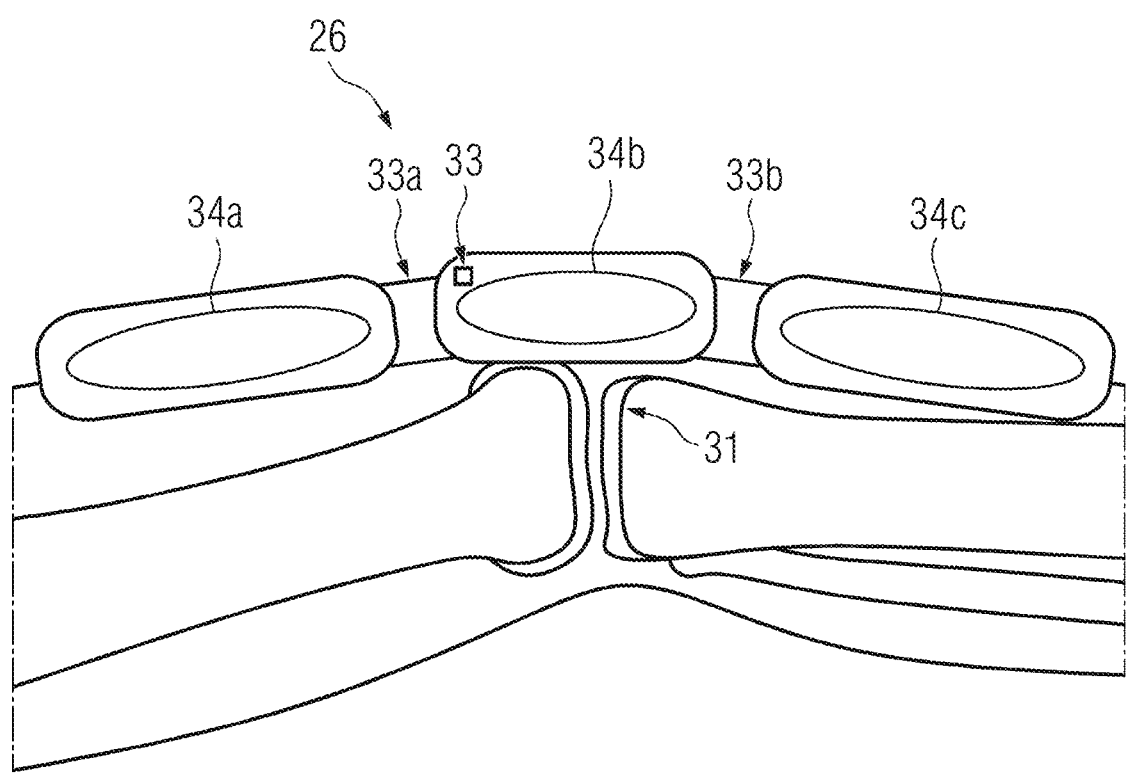
FIG. 4 illustrates an embodiment of a local coil according to the disclosure.

FIG. 4 shows a further embodiment of the local coil 26 according to the disclosure. In this example, the local coil 26 includes a plurality of antenna elements 34*a*, 34*b* and 34*c* (34*a*-*c*), which are positioned on the knee joint 31 of the patient 15. The local coil 26 further includes at least one sensor 33 with at least one flexible sensor element 33*a*, 33*b*. The at least one flexible sensor element 33*a*, 33*b* constitutes a reversibly deformable section of the local coil 26, which is deformed as a result of movement of the knee joint 31. In this case, the local coil 26 can e.g. be designed as a lay-on coil which is laid on a surface of the patient 15. For instance, a weight force of the local coil 26 is sufficient to deform the at least one flexible sensor element 33*a*, 33*b* upon the bending and/or stretching of the knee joint 31. However, it is obviously also conceivable for the local coil 26 to include at least one support element 32, which holds the local coil 26 and/or an antenna element 34*a*-*c* in a position according to the application on the knee joint 31 of the patient 15.

Figure 5:
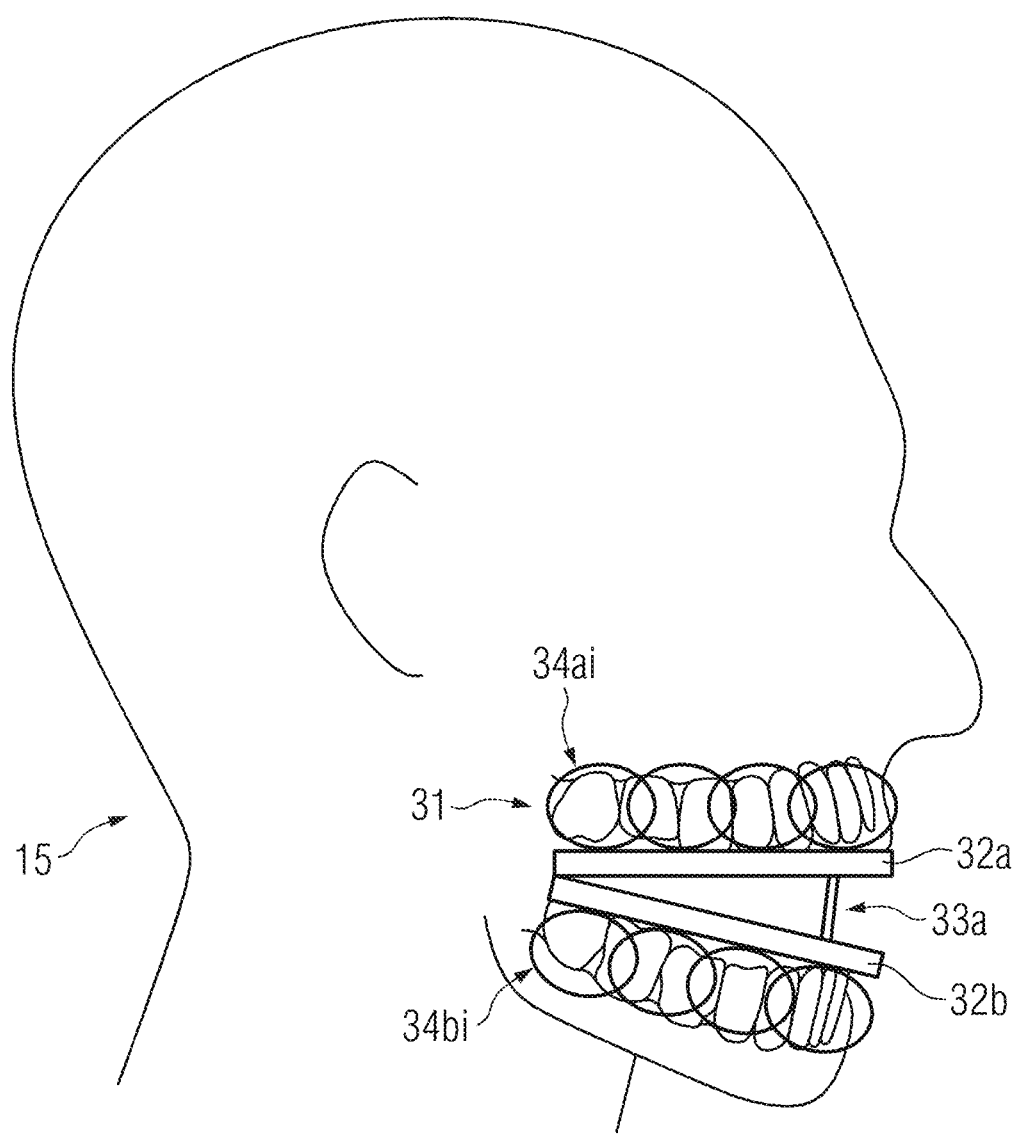
FIG. 5 illustrates an embodiment of a local coil according to the disclosure.

FIG. 5 shows a further embodiment of the local coil 26 according to the disclosure. The local coil 26 is positioned on the jaw region 31 of the patient 15. The local coil 26 further includes two support elements 32*a* and 32*b*, which hold a plurality of antenna elements 34*ai* and a plurality of antenna elements 34*bi* in a position according to the application on an upper dental arch and on a lower dental arch of the patient 15. In the example shown, the at least one sensor 33 includes a flexible sensor element 33*a* mechanically connected to the support element 32*a* on the upper dental arch and the support element 32*b* on the lower dental arch. For instance, the flexible sensor element 33*a* can be connected to the support element 32*a* on a first section and to the support element 32*b* on a second section. Thus, the flexible sensor element 33*a* can be deformed as a result of a relative movement between the upper dental arch and the lower dental arch. In this embodiment, the support elements 32a and 32b may be designed as bite splints embodied to be positioned on a dental arch of the patient 15.

Figure 6:
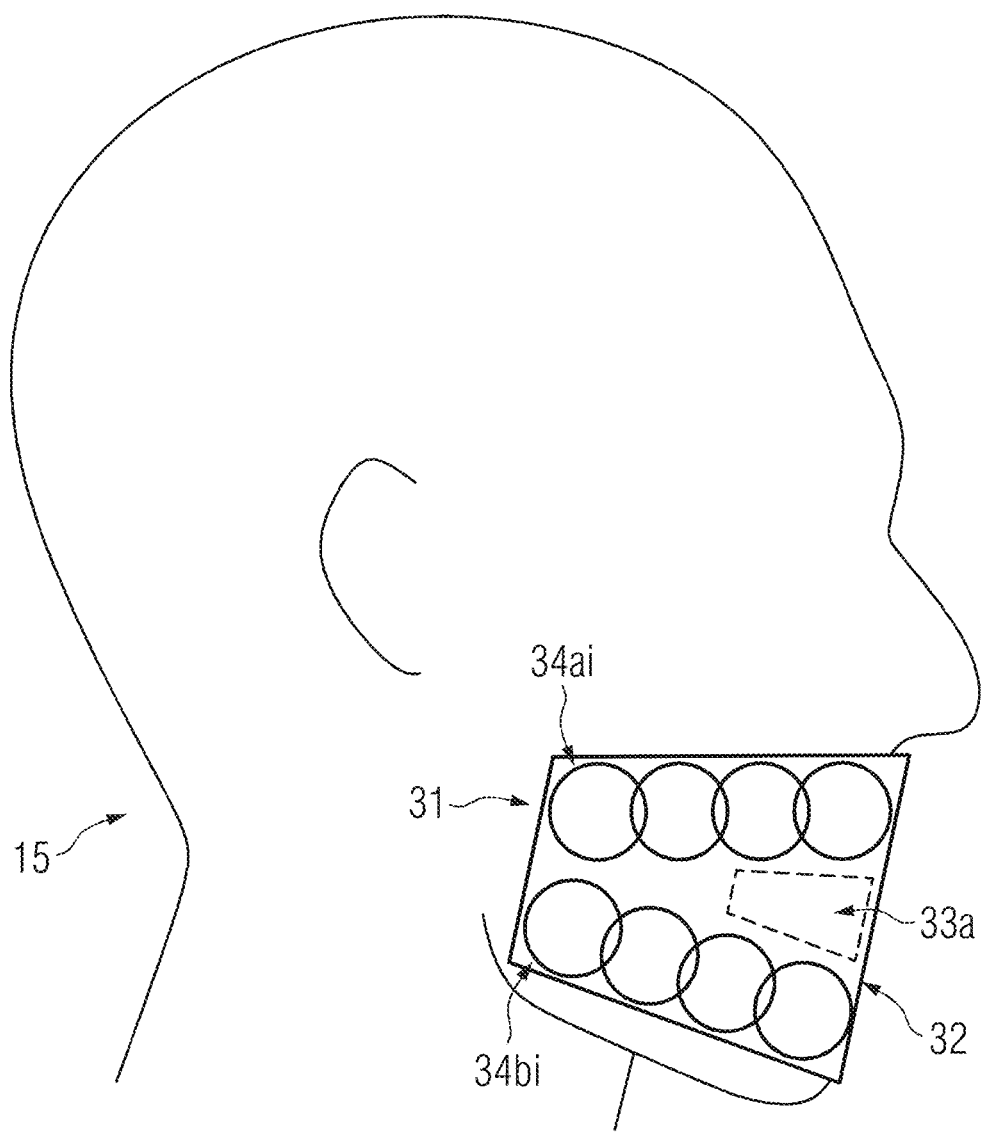
FIG. 6 illustrates an embodiment of a local coil according to the disclosure.

FIG. 6 shows a further embodiment of the local coil 26 according to the disclosure. In this case, the support element 32 takes the form of a face mask embodied to hold the local coil 26 on a surface of the jaw region 31 of the patient 15. The support element 32 further holds the plurality of antenna elements 34ai in a position according to the application on the patient's upper dental arch and the plurality of antenna elements 34bi on the patient's lower dental arch 15. On the other hand, the flexible sensor element 33a of the at least one sensor 33 is positioned between the upper dental arch and the lower dental arch in an oral cavity of the patient 15. In this case, a first section of the flexible sensor element 33a can be positioned on the upper dental arch, while a second section of the flexible sensor element 33a is positioned on the lower dental arch. The flexible sensor element 33a can e.g. be embodied as a bite piece, which is deformed as a result of a relative movement of the upper dental arch and the lower dental arch of the patient 15. The flexible sensor element 33a can be connected to the at least one sensor 33 and/or the local coil 26 by means of an electrical signal connection (not shown). The electrical signal connection between the flexible sensor element 33a and the at least one sensor 33 and/or the local coil 36 can e.g. be guided out of the oral cavity to the outside between closed lips of the patient 15. However, it is likewise conceivable for the at least one sensor 33 and/or the flexible sensor element 33a to be embodied to transmit the information on the movement of the diagnostically relevant position of the patient 15 wirelessly to the magnetic resonance imaging system 10.

FIG. 7 shows a possible flow chart of a method according to the disclosure for correcting patient movement 15 during an imaging examination by means of an imaging apparatus 10 with at least one sensor 33 and a correction unit 37.

In a step S1, the at least one sensor 33 is positioned on a diagnostically relevant body region 31 of the patient 15. In this case, the at least one sensor 33 can, for example, be positioned as shown in FIG. 4 by means of a lay-on coil 26 on the diagnostically relevant body region 31. However, it is likewise conceivable for the at least one sensor 33 to be held on the diagnostically relevant body region 31 as shown in FIG. 3 by a support element 32a, 32b and/or 32c. The at least one sensor 33 may be positioned on the diagnostically relevant body region 31 during preparation for the imaging examination. In addition to the embodiments shown in FIGS. 1 to 6, there are obviously further conceivable possibilities for positioning the at least one sensor 33 according to an above-described embodiment.

In a step S2, the patient 15 is positioned in an image recording region of the imaging apparatus 10. In this case, as shown in FIG. 1, the patient 15 can be moved into an image recording area 14 of the imaging apparatus 10 by means of a patient table 17. However, it is also conceivable for the imaging apparatus 10 to be embodied as a dedicated scanner that is matched to an imaging examination of the diagnostically relevant body region 31 of the patient 15 and/or can be positioned relative to the diagnostically relevant body region 31 in a position according to the application for an imaging examination of the diagnostically relevant body region 31. Further, the positioning of the patient 15 in the image recording region can already comprise calibration, synchronization and/or testing of a function of the at least one sensor 33 and/or a transmitter-receiver arrangement.

In a further step S3, the imaging examination for acquiring image data from the diagnostically relevant body region 31 of the patient 15 is performed. The acquisition of image data can, for example, comprise the acquisition of magnetic resonance signals from the diagnostically relevant body region 31 of the patient 15. However, it is likewise conceivable for the acquisition of image data to involve the acquisition of photons or X-rays by means of a suitable detector of the imaging apparatus 10. Accordingly, the acquisition of the image data can comprise the acquisition of magnetic resonance image data, computed tomography image data and image data from other imaging modalities.

In a step S4, the signal from the at least one sensor 33 is acquired. The step of the acquisition of the signal from the at least one sensor 33 and the performance of the imaging examination, e.g. the acquisition of the image data from the diagnostically relevant body region 31 of the patient 15 may at least partially overlap. In this case, the signal from the at least one sensor 33 may be transmitted to the computing unit 28, the control unit 22 and/or the correction unit 37 of the imaging apparatus 10 by means of a wired or wireless connection.

In one embodiment, the imaging apparatus 10 is a magnetic resonance imaging system 10, wherein the signal from the at least one sensor 33 is modulated onto a magnetic resonance signal acquired by means of an antenna element 34. In this case, the local coil 26 and/or the at least one sensor 33 can include an electronic circuit with a modulation unit, which modulates the signal from the at least one sensor 33 onto the acquired magnetic resonance signal from the antenna element 34. The magnetic resonance imaging system 10, e.g. the correction unit 37, can include a demodulation unit, which extracts the signal from the at least one sensor 33 from the modulated magnetic resonance signal. The electronic circuit can likewise wirelessly transmit the signal from the at least one sensor 33 to the imaging apparatus 10. In a magnetic resonance imaging system 10, the signal can e.g. be present in a frequency and power range of a magnetic resonance signal such that the signal can be received directly by the receiving unit of the magnetic resonance imaging system 10.

In one embodiment, the acquisition of the signal from the at least one sensor 33 comprises acquiring a second signal from a second sensor and/or a third signal from a third sensor. In this case, the second sensor and the third sensor use a measuring principle which differs from that of the at least one sensor 33. In this case, the second signal and/or the third signal provide information on a movement of the diagnostically relevant body region 31, which is used in the correction method. In one example, the second sensor is a Hall sensor and the third sensor is a sensor of a transmitter-receiver arrangement according to an above-described embodiment. However, the second sensor and/or the third sensor can also be designed as a gyro sensor, an acceleration sensor, a bending sensor, a distance sensor and/or as a fiber optic sensor.

In a further step S5, a correction method is performed by means of the correction unit 37 in dependence on the signal from the at least one sensor, wherein the correction method reduces the influence of the movement of the diagnostically relevant body region 31 of the patient 15 on the imaging examination. The performance of the correction method can comprise performing at least one of the following methods:
  motion gating,
  outputting feedback regarding the movement of the diagnostically relevant body region to the patient by means of an output unit, a prospective and/or retrospective correction method.

In one example, as shown in FIG. 2, the eyeglasses 32 of the patient 15 have an output unit, such as, for example, a display, an active control element and/or a loudspeaker, which provide the patient 15 with feedback on movement of the diagnostically relevant body region 31. Thus, the patient 15 can be informed that movement of the diagnostically relevant body region 31 is unfavorable for the performance of the imaging examination. However, it is likewise conceivable for the patient 15 to be informed of the extent of an involuntary movement, such as, for example, a tongue movement, a swallowing movement and/or a respiratory movement. Thus, the patient 15 can attempt to counteract the movement accordingly, taking into account the information from the output unit. It is also conceivable for the output unit to be embodied to transmit a movement instruction or a message from a user of the imaging apparatus 10 to the patient.

In an optional step S6, individual images of the upper dental arch and the lower dental arch of the patient 15 are reconstructed in dependence on acquired magnetic resonance signals from the upper dental arch and the lower dental arch and the individual images of the upper dental arch and the lower dental arch are merged to form one image in an image space. In this case, the imaging apparatus 10 can e.g. be designed as a magnetic resonance imaging system 10 according to FIG. 2, wherein the local coil 26 is positioned on a jaw region 31 of the patient 15 and has a plurality of antenna elements 34ai, 34bi (see FIG. 6), wherein a first antenna element is positioned on an upper dental arch of the patient 15 and a second antenna element is positioned on a lower dental arch of the patient 15. In this case, the performance of the imaging examination comprises receiving magnetic resonance signals from the lower dental arch by means of the second antenna element and receiving magnetic resonance signals from the upper dental arch by means of the first antenna element. The performance of the correction method comprises motion gating, wherein magnetic resonance signals from the lower dental arch and/or the upper dental arch are acquired in dependence on the at least one sensor 33 by means of the local coil 26. It is e.g. conceivable for the acquisition of magnetic resonance signals by means of the second antenna element to be suspended upon movement of the lower jaw that is detected by means of the at least one sensor 33 with the flexible sensor element 33a. On the other hand, magnetic resonance signals from the first antenna element can be acquired continuously since movement of the lower jaw typically has a negligible impact on the position of the upper dental arch of the patient 15. The magnetic resonance signals acquired from the first antenna element and the second antenna element can then be used to reconstruct a single image of the upper dental arch and a single image of the lower dental arch, which can be merged in an image space to form an image of the jaw region 31 of the patient 15.

Obviously, the embodiments of the method according to the disclosure, the imaging apparatus according to the disclosure and the local coil according to the disclosure described here are to be understood as being exemplary only. Individual embodiments can be expanded by features of other embodiments. The sequence of the method steps of the method according to the disclosure should be understood as being exemplary only. The individual steps can also be performed in another sequence or can partially or completely overlap in time.

The various components described herein may be referred to as "units." Such components may be implemented via any suitable combination of parts, components, hardware, and/or software components as applicable and/or known to achieve the intended functionality of the respective units. Again, this may include mechanical and/or electrical components, FPGAs, processors, processing circuitry, or other suitable hardware components configured to execute instructions or computer programs that are stored on a suitable computer readable medium. Regardless of the particular implementation, such units when applicable and relevant may alternatively be referred to herein as "circuitry," "processors," or "processing circuitry."

What is claimed is:

1. An imaging apparatus for acquiring image data from a diagnostically-relevant body region of a patient, comprising:
   a sensor configured to output a signal containing information on a movement of the diagnostically-relevant body region of the patient, the sensor being a non-imaging sensor, and the signal being based upon the movement of the diagnostically-relevant body region of the patient;
   correction circuitry configured to apply a correction technique based upon on the signal received from the sensor to reduce an influence of the movement of the diagnostically-relevant body region of the patient on an imaging examination; and
   a transmitter-receiver system comprising the sensor, the transmitter-receiver system comprising a transmitter configured to transmit a reference signal and a receiver configured to receive the reference signal,
   wherein the transmitter and/or the receiver is positioned according to an application in a patient receiving region of the imaging apparatus such that a signal property of the reference signal between the transmitter and the receiver is correlated with the movement of the diagnostically-relevant body region of the patient,
   wherein the imaging apparatus is configured to ascertain the movement of the diagnostically-relevant body region of the patient via the sensor based upon the received reference signal, and
   wherein the reference signal is an ultrasound signal and/or a radio-frequency signal in a frequency and power range corresponding to a magnetic resonance measurement.

2. The imaging apparatus as claimed in claim 1, wherein the imaging apparatus is a magnetic resonance imaging system, and further comprising:
   a local coil positioned according to an application on the diagnostically-relevant body region of the patient, and configured to receive magnetic resonance signals in a frequency and power range corresponding to a magnetic resonance measurement,
   wherein the local coil includes the sensor, and
   wherein the sensor is configured as an acceleration sensor, a gyro sensor, and/or a Hall sensor.

3. The imaging apparatus as claimed in claim 1, wherein the sensor comprises a flexible sensor element positioned according to an application on the diagnostically relevant body region of the patient, the sensor being configured to be deformed as a result of movement of the diagnostically-relevant body region of the patient, and
   wherein the imaging apparatus is configured to ascertain the movement of the diagnostically-relevant body region of the patient via the sensor based upon a deformation of the flexible sensor element.

4. The imaging apparatus as claimed in claim 3, further comprising:

a support element that is mechanically connected to the flexible sensor element, the support element being configured to hold the flexible sensor element in a position according to the application on the diagnostically-relevant body region of the patient, wherein the support element and the flexible sensor element are configured to be positioned relative to one another with respect to a movement of the diagnostically-relevant body region of the patient with a deformation of the flexible sensor element, and wherein the imaging apparatus is configured to ascertain the movement of the diagnostically-relevant body region of the patient via the sensor based upon the relative movement of the support element and the flexible sensor element.

5. The imaging apparatus as claimed in claim 4, further comprising:

a further support element that is connected to the support element via the flexible sensor element, wherein the support element and the further support element are positioned according to an application on opposite body regions on a joint of the patient, wherein the flexible sensor element is configured to be deformed as a result of movement of the joint, and wherein the imaging apparatus is configured to ascertain the movement of the joint via the sensor based upon the deformation of the flexible sensor element.

6. The imaging apparatus as claimed in claim 3, wherein the imaging apparatus is a magnetic resonance imaging system, and further comprising:

a local coil, which includes the sensor with the flexible sensor element, the local coil being configured to receive magnetic resonance signals in a frequency and power range of a magnetic resonance measurement, wherein at least one section of the local coil with the flexible sensor element is reversibly deformable, and wherein the sensor is configured to output a signal correlated with the deformation of the flexible sensor element.

7. The imaging apparatus as claimed in claim 1, wherein the reference signal is a radio-frequency signal within a frequency range of 1 MHz to 500 MHz, and wherein magnetic resonance signals used for the magnetic resonance measurement are within the frequency range of 1 MHz to 500 MHz.

8. An imaging apparatus for acquiring image data from a diagnostically-relevant body region of a patient, comprising:

a sensor configured to output a signal containing information on a movement of the diagnostically-relevant body region of the patient, the sensor being a non-imaging sensor, and the signal being based upon the movement of the diagnostically-relevant body region of the patient; and correction circuitry configured to apply a correction technique based upon on the signal received from the sensor to reduce an influence of the movement of the diagnostically-relevant both region of the patient on an imaging examination, wherein:

the sensor comprises a flexible sensor element positioned according to an application on the diagnostically relevant body region of the patient, the sensor being configured to be deformed as a result of movement of the diagnostically-relevant body region of the patient, the imaging apparatus is configured to ascertain the movement of the diagnostically-relevant body region of the patient via the sensor based upon a deformation of the flexible sensor element, the flexible sensor element is positioned according to an application on a dental arch of the patient, the flexible sensor element being configured to be deformed as a result of a movement of a lower jaw of the patient, and the imaging apparatus is configured to ascertain movement of the lower jaw via the sensor based upon the deformation of the flexible sensor element.

9. A method for correcting a patient movement during an imaging examination via an imaging apparatus with at least one sensor and correction circuitry, the method comprising:

outputting, via the at least one sensor, a signal containing information on movement of a diagnostically-relevant body region of the patient, the at least one sensor comprising a non-imaging sensor;

positioning the patient in an image recording region of the imaging apparatus;

performing the imaging examination for acquiring image data from the diagnostically-relevant body region of the patient;

acquiring the signal from the at least one sensor; and performing a correction technique via the correction circuitry based upon the signal acquired from the at least one sensor to reduce an influence of the movement of the diagnostically-relevant body region of the patient on the imaging examination, wherein the imaging apparatus is a magnetic resonance imaging system with a local coil, and wherein the signal from the at least one sensor is modulated onto a magnetic resonance signal acquired via the local coil.

10. The method as claimed in claim 9, wherein the act of acquiring the signal from the at least one sensor comprises:

acquiring a further signal from a further sensor, wherein the further sensor is a non-imaging sensor and uses a measuring principle that is different from that of the at least one sensor, wherein the further signal contains information on movement of the diagnostically-relevant body region of the patient, and wherein performance of the correction technique is based upon the signal acquired from the at least one sensor and the further signal acquired from the further sensor.

11. The method as claimed in claim 9, wherein performance of the correction technique comprises performing at least one of:

motion gating;

outputting feedback regarding the movement of the diagnostically-relevant body region to the patient via output circuitry;

a prospective correction technique; and a retrospective correction technique.

12. A method for correcting a patient movement during an imaging examination via an imaging apparatus with at least one sensor and correction circuitry, the method comprising:

outputting, via the at least one sensor, a signal containing information on movement of a diagnostically-relevant body region of the patient, the at least one sensor comprising a non-imaging sensor;

positioning the patient in an image recording region of the imaging apparatus;

performing the imaging examination for acquiring image data from the diagnostically-relevant body region of the patient;

acquiring the signal from the at least one sensor;

performing, a correction technique via the correction circuitry based upon the signal acquired from the at least one sensor to reduce an influence of the movement of the diagnostically-relevant body region of the patient on the imaging examination;

positioning a local coil on a jaw region of the patient, the local coil including a plurality of antenna elements, wherein:
a first antenna element from among the plurality of antenna elements is positioned on an upper dental arch of the patient, and a second antenna element from among the plurality of antenna elements is positioned on a lower dental arch of the patient,
the performing the imaging examination comprises:
receiving magnetic resonance signals from the lower dental arch and the upper dental arch via the plurality of antenna elements, and
the performing the correction technique comprises performing motion gating, magnetic resonance signals from the lower dental arch and/or the upper dental arch are acquired based upon the at least one sensor via the local coil;
reconstructing individual images of the upper dental arch and the lower dental arch of the patient based upon the received magnetic resonance signals from the upper dental arch and the lower dental arch; and
merging the individual images of the upper dental arch and the lower dental arch to form one image in an image space.

13. A non-transitory computer-readable medium having instructions stored thereon that, when executed by one or more processors of an imaging apparatus that includes at least one sensor and correction circuitry, cause the imaging apparatus to correct for a patient movement during an imaging examination via the imaging apparatus by:
outputting, via the at least one sensor, a signal containing information on movement of a diagnostically-relevant body region of the patient, the at least one sensor comprising a non-imaging sensor;
positioning the patient in an image recording region of the imaging apparatus;
performing the imaging examination for acquiring image data from the diagnostically-relevant body region of the patient;
acquiring the signal from the at least one sensor; and
performing a correction technique via the correction circuitry based upon the signal acquired from the at least one sensor to reduce an influence of the movement of the diagnostically-relevant body region of the patient on the imaging examination, wherein the imaging apparatus is a magnetic resonance imaging system with a local coil, and
wherein the instructions, when executed by the one or more processors of the imaging apparatus, further cause the imaging apparatus to correct for the patient movement by modulating the signal from the at least one sensor onto a magnetic resonance signal acquired via the local coil.

14. The non-transitory computer-readable medium as claimed in claim 13, wherein the instructions further cause the imaging apparatus to acquire the signal from the at least one sensor by acquiring a further signal from a further sensor,
wherein the further sensor is a non-imaging sensor and uses a measuring principle that is different from that of the at least one sensor,
wherein the further signal contains information on movement of the diagnostically-relevant body region of the patient, and
wherein performance of the correction technique is based upon the signal acquired from the at least one sensor and the further signal acquired from the further sensor.

15. The non-transitory computer-readable medium as claimed in claim 13, wherein the instructions further cause the imaging apparatus to perform the correction technique by performing at least one of:
motion gating;
outputting feedback regarding the movement of the diagnostically-relevant body region to the patient via output circuitry;
a prospective correction technique; and
a retrospective correction technique.

16. The non-transitory computer-readable medium as claimed in claim 13, wherein the imaging apparatus is a magnetic resonance imaging system, and further including instructions that, when executed by the one or more processors, cause the imaging apparatus to correct for the patient movement during an imaging examination via the imaging apparatus by:
positioning the local coil on a jaw region of the patient, the local coil including a plurality of antenna elements, wherein a first antenna element from among the plurality of antenna elements is positioned on an upper dental arch of the patient, and a second antenna element from among the plurality of antenna elements is positioned on a lower dental arch of the patient;
perform the imaging examination by:
receiving the magnetic resonance signals from the lower dental arch and the upper dental arch via the plurality of antenna elements,
wherein the act of performing the correction technique comprises performing motion gating,
wherein magnetic resonance signals from the lower dental arch and/or the upper dental arch are acquired based upon the at least one sensor via the local coil;
reconstruct individual images of the upper dental arch and the lower dental arch of the patient based upon the acquired magnetic resonance signals from the upper dental arch and the lower dental arch; and
merge the individual images of the upper dental arch and the lower dental arch to form one image in an image space.

* * * * *